United States Patent
Shibamoto et al.

(10) Patent No.: US 9,168,026 B2
(45) Date of Patent: Oct. 27, 2015

(54) ULTRASONIC DIAGNOSTIC APPARATUS, PHASE SHIFT TRANSMISSION/RECEPTION CONTROL METHOD, AND ULTRASONIC PROBE

(71) Applicants: Koichi Shibamoto, Nasushiobara (JP); Takashi Takeuchi, Otawara (JP); Satoru Tezuka, Nasushiobara (JP)

(72) Inventors: Koichi Shibamoto, Nasushiobara (JP); Takashi Takeuchi, Otawara (JP); Satoru Tezuka, Nasushiobara (JP)

(73) Assignees: KABUSHIKI KAISHA TOSHIBA, Tokyo (JP); Toshiba Medical Systems Corporation, Otawara-shi (JP)

(*) Notice: Subject to any disclaimer, the term of this patent is extended or adjusted under 35 U.S.C. 154(b) by 58 days.

(21) Appl. No.: 13/706,583

(22) Filed: Dec. 6, 2012

(65) Prior Publication Data

US 2013/0190625 A1   Jul. 25, 2013

(30) Foreign Application Priority Data

Jan. 23, 2012   (JP) ................................. 2012-011423

(51) Int. Cl.
*A61B 8/00*   (2006.01)
*G01S 7/52*   (2006.01)
(Continued)

(52) U.S. Cl.
CPC ............... *A61B 8/4488* (2013.01); *A61B 8/145* (2013.01); *A61B 8/4444* (2013.01); *A61B 8/54* (2013.01); *A61B 8/546* (2013.01); *G01S 7/5205* (2013.01); *A61B 8/06* (2013.01); *A61B 8/0883* (2013.01); *A61B 8/4281* (2013.01); *A61B 8/4483* (2013.01);
(Continued)

(58) Field of Classification Search
CPC .... A61B 8/4488; A61B 8/145; A61B 8/4444; A61B 8/54; A61B 8/546; A61B 8/4281

USPC ............................................................. 600/447
See application file for complete search history.

(56) References Cited

U.S. PATENT DOCUMENTS 4,628,223 A * 12/1986 Takeuchi et al. ............... 310/358
4,672,591 A *  6/1987 Breimesser et al. ........... 367/152
(Continued)

FOREIGN PATENT DOCUMENTS

CN   101444430 A   6/2009
EP    1 728 563 A3  12/2006
(Continued)

OTHER PUBLICATIONS

The Extended European Search Report issued May 7, 2013, in Application No. / Patent No. 12196790.5-1812.
(Continued)

*Primary Examiner* — Bo J Peng
(74) *Attorney, Agent, or Firm* — Oblon, McClelland, Maier & Neustadt, L.L.P.

(57) ABSTRACT

According to one embodiment, an ultrasonic probe has a laminated structure of an acoustic matching layer, transducer layer with arrayed transducers, and backing layer. A transmission/reception unit transmits and receives ultrasonic waves to and from an object via the transducers. A control unit controls the transmission/reception unit to synchronize ultrasonic-wave generation by a specific transducer of the transducers with ultrasonic-wave reception by a different transducer. A phase shift detection unit detects a phase shift between an output signal from the transmission/reception unit and a reference signal, the output signal corresponding to synchronization between the ultrasonic-wave generation and the ultrasonic-wave reception.

8 Claims, 8 Drawing Sheets

(51) Int. Cl.
*A61B 8/14* (2006.01)
*A61B 8/06* (2006.01)
*A61B 8/08* (2006.01)

(52) U.S. Cl.
CPC .............. *A61B 8/485* (2013.01); *A61B 8/488* (2013.01); *B06B 2201/40* (2013.01); *B06B 2201/55* (2013.01); *B06B 2201/76* (2013.01)

(56) References Cited

U.S. PATENT DOCUMENTS

| 4,806,193 | A | * | 2/1989 | Von Raben et al. | 156/378 |
| 6,225,729 | B1 | * | 5/2001 | Izumi et al. | 310/334 |
| 2004/0258127 | A1 | * | 12/2004 | Ramamurthy et al. | 374/117 |
| 2007/0087311 | A1 | * | 4/2007 | Garvey et al. | 434/21 |

FOREIGN PATENT DOCUMENTS

| JP | 3863234 | 10/2006 |
| WO | WO 2011/033454 A1 | 3/2011 |

OTHER PUBLICATIONS

Chinese Office Action issued May 4, 2014, in China Patent application No. 201210444663.3 (with English translation).

* cited by examiner

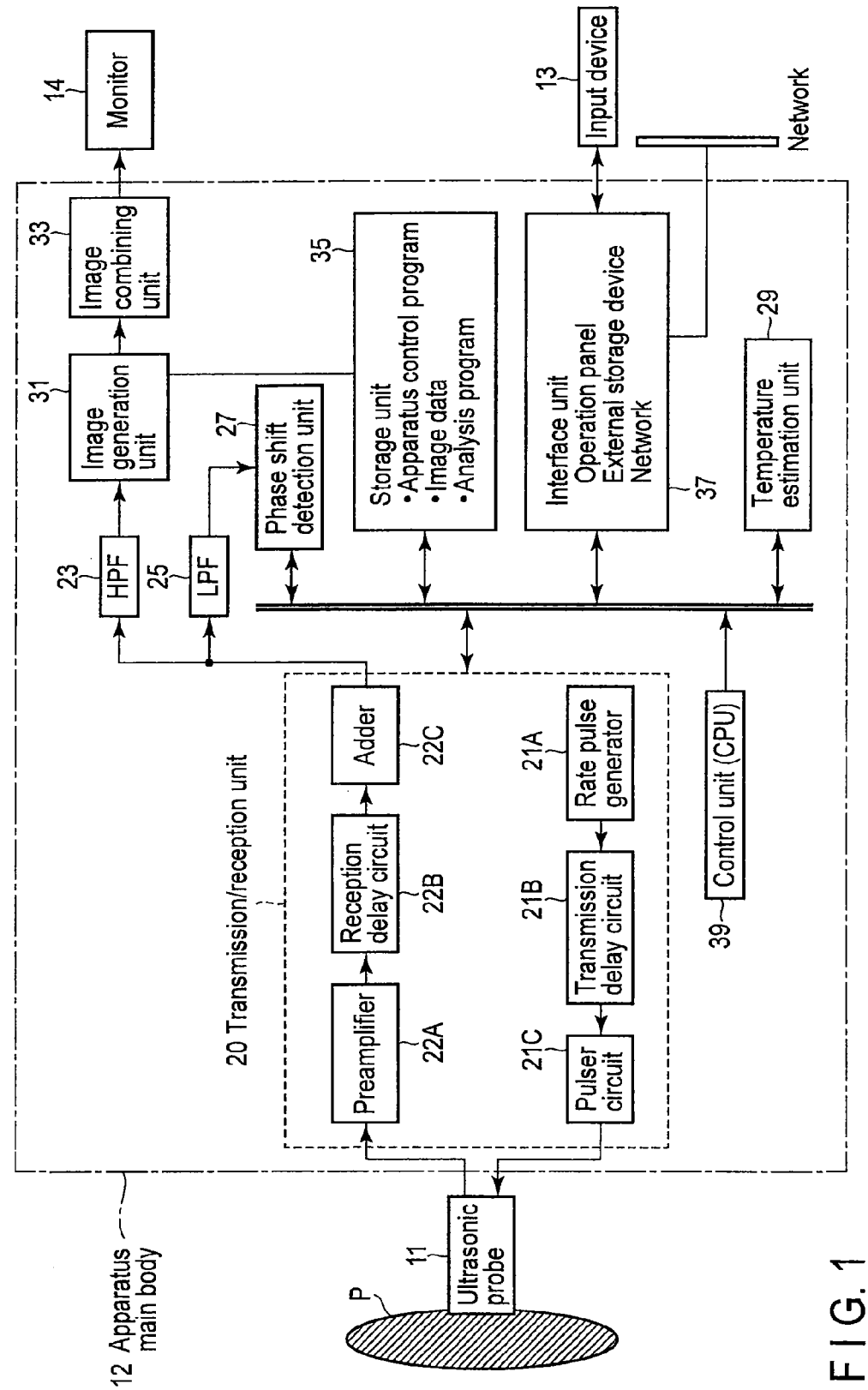
F I G. 1

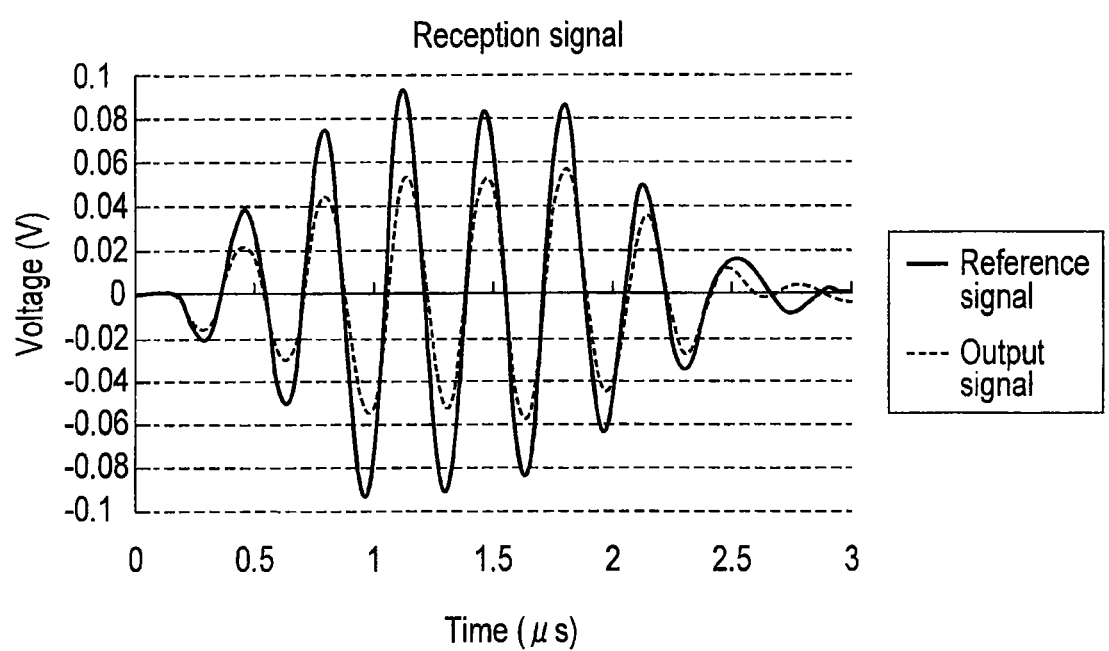
F I G. 6

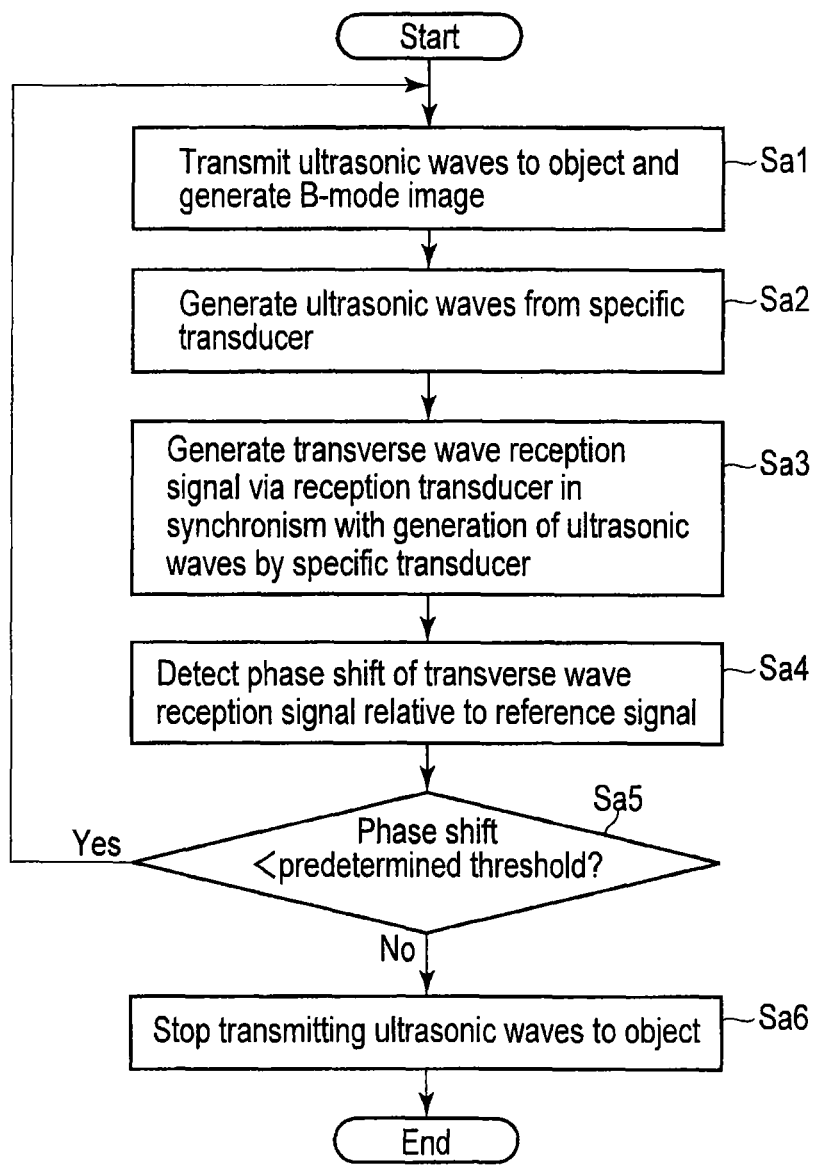
F I G. 7

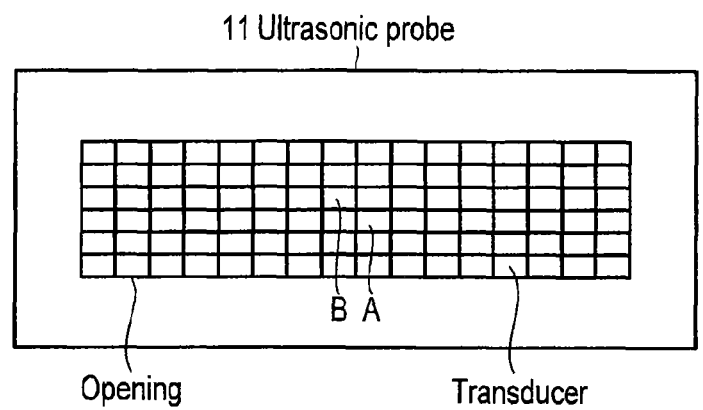
F I G. 8
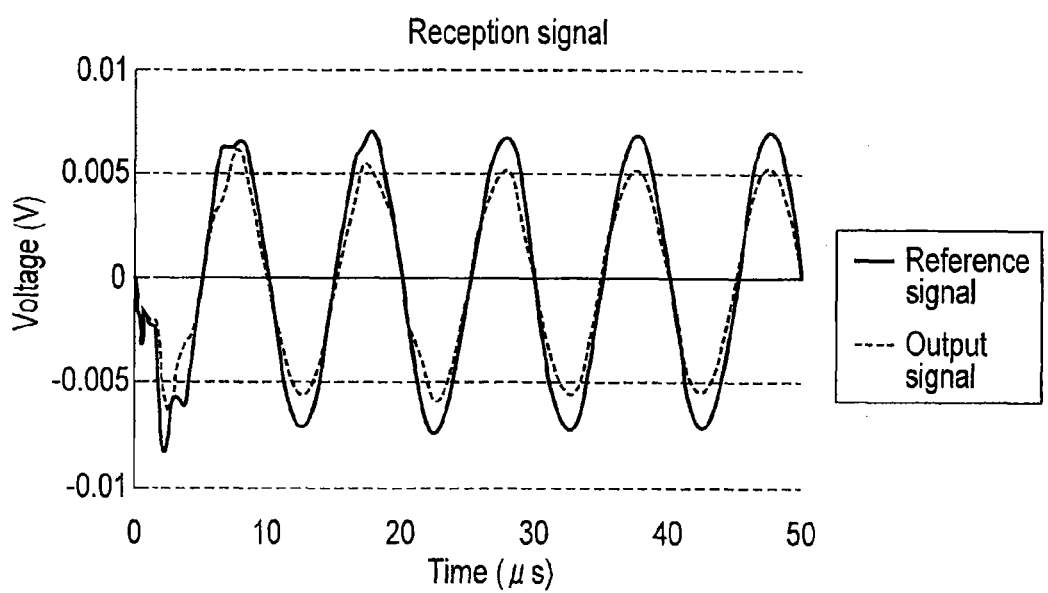
F I G. 9

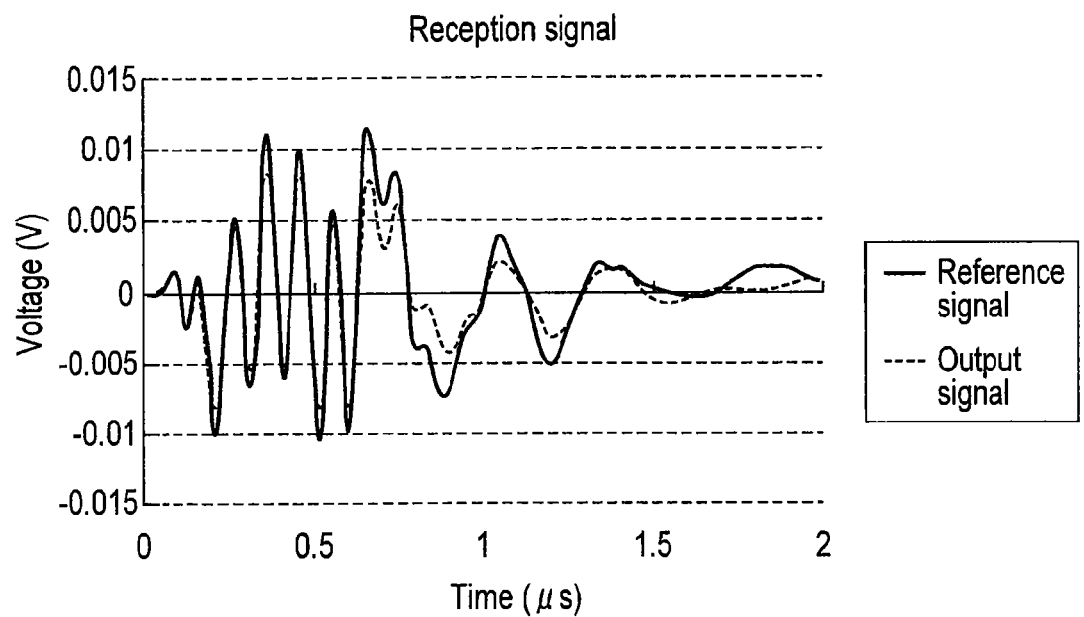
F I G. 10
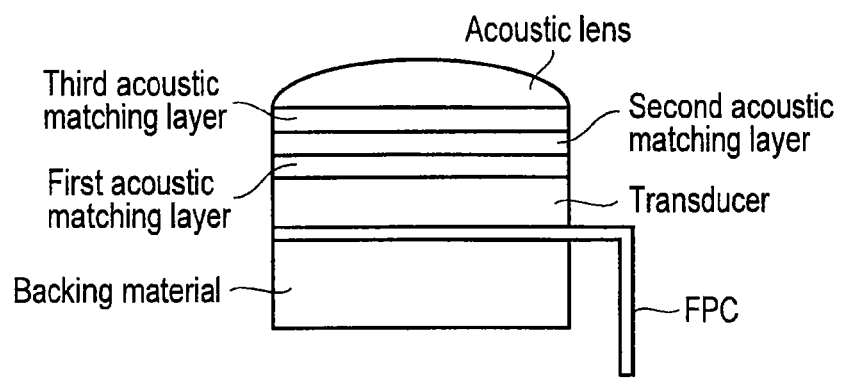
F I G. 11

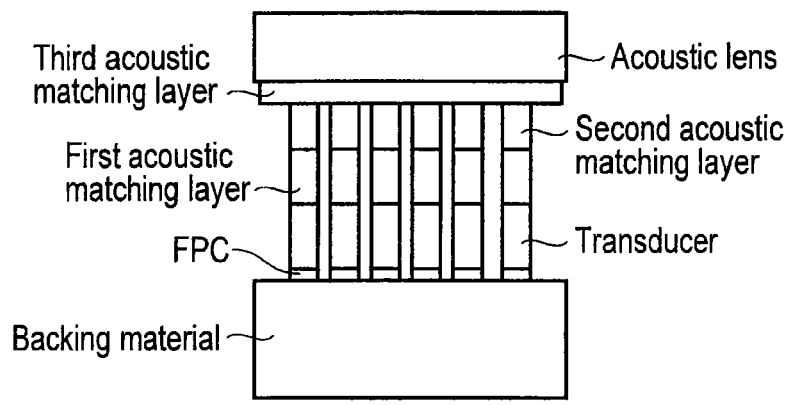
F I G. 1 2
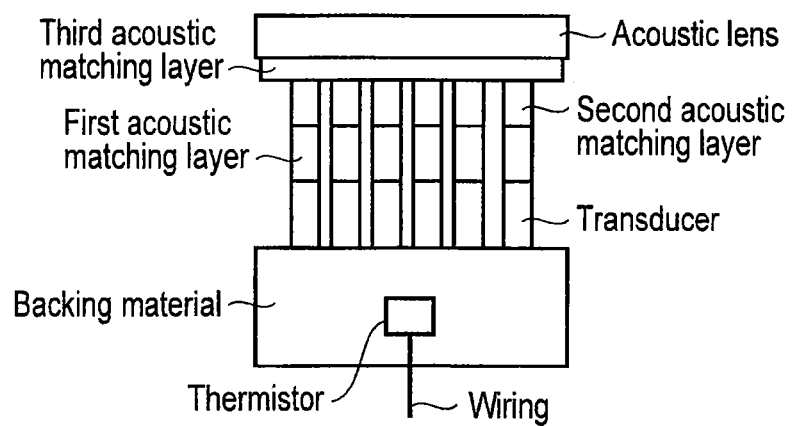
F I G. 1 3

ULTRASONIC DIAGNOSTIC APPARATUS, PHASE SHIFT TRANSMISSION/RECEPTION CONTROL METHOD, AND ULTRASONIC PROBE

CROSS-REFERENCE TO RELATED APPLICATIONS

This application is based upon and claims the benefit of priority from Japanese Patent Application No. 2012-011423, filed Jan. 23, 2012, the entire contents of which are incorporated herein by reference.

FIELD

Embodiments described herein relate generally to an ultrasonic diagnostic apparatus, a phase shift transmission/reception control method, and an ultrasonic probe.

BACKGROUND

Conventionally, an ultrasonic diagnostic apparatus can scan the interior of an object with ultrasonic waves and visualize the internal state of the object based on the reception signal generated from reflected waves from inside the object. More specifically, the ultrasonic diagnostic apparatus transmits ultrasonic waves into the object via the ultrasonic probe. The ultrasonic diagnostic apparatus generates a reception signal by receiving, via the ultrasonic probe, reflected waves from inside the object which are generated by acoustic impedance mismatching inside the object. The ultrasonic diagnostic apparatus visualizes the internal state of the object based on the reception signal.

Conventionally, as shown in FIGS. 11 and 12, an ultrasonic probe includes a plurality of transducers which are arranged in an array form and generate ultrasonic waves, a plurality of acoustic matching layers which alleviate the acoustic impedance mismatching between the transducers and an object from the transducers to the object contact surface side, and an acoustic lens which focus ultrasonic waves. The ultrasonic probe also includes an FPC (Flexible Printed Circuit) for signal extraction and a backing material, which are provided on the transducer rear surface side. Each of the plurality of transducers vibrates to generate ultrasonic waves based on a transmission signal from the ultrasonic diagnostic apparatus.

The temperature of a portion of the ultrasonic probe which comes into contact with an object (to be referred to as an object contact portion hereinafter) generally rises as each transducer is driven. In general, proper driving conditions are set for the ultrasonic diagnostic apparatus. If, however, the apparatus keeps generating heat in an unexpected way due to some kind of abnormality, a burn injury or the like may be inflicted on the object.

Under the circumstances, several techniques have been proposed from the viewpoint of an improvement in product safety as follows. As shown in FIG. 13, there has been provided a technique of detecting the temperature of an object contact portion at the time of driving of ultrasonic waves by disposing a temperature sensor such as a thermistor in the ultrasonic probe. At this time, a temperature sensor such as a thermistor influences the propagation of ultrasonic waves, and hence is disposed in a backing material. In this case, the ultrasonic diagnostic apparatus can detect abnormal heat generation and stop driving the transducers by monitoring the temperature of the backing material using the signals output from the thermistor.

It is however necessary to extract a signal line for the thermistor from inside the ultrasonic probe separately from an ultrasonic signal line. The extraction of a signal line of the thermistor complicates the manufacture of an ultrasonic probe, and hence increases the manufacturing cost. In addition, the temperature monitored by signals from the thermistor is the temperature of the backing material but is not the temperature of the object contact portion. That is, the above technique does not directly monitor the temperature of the object contact portion in terms of temporal and spatial detection accuracy, and is an indirect temperature monitoring system.

There has also been proposed a technique of identifying the unused state of an ultrasonic probe by disposing a pressure sensor outside the ultrasonic probe. The main purpose of this technique is to prevent a deterioration in the quality of a product by stopping driving the ultrasonic probe during an unused period. The technique can also contribute to an improvement in product safety by reducing unnecessary heat generation.

It is however necessary to extract a signal line of the pressure sensor separately from an ultrasonic signal line. This poses the same problem as that in the prior art. In addition, this technique cannot cope with heat generation abnormality caused during the use of the ultrasonic probe.

BRIEF DESCRIPTION OF THE DRAWINGS

FIG. 1 is a block diagram showing the arrangement of an ultrasonic diagnostic apparatus according to this embodiment.

FIG. 6 is a graph showing a simulation result to be compared with that in FIG. 5, and showing an output signal (80° C.) at the time of transmission of five waves of ultrasonic waves having a frequency of 3 MHz, together with a reference signal (25° C.) according to this embodiment.

FIG. 7 is a flowchart showing a procedure for detecting a phase shift of an output signal relative to a reference signal and stopping the transmission of ultrasonic waves to an object if the detected phase shift is equal to or more than a predetermined threshold according to this embodiment.

FIG. 8 is a view showing an example of a specific transducer and reception transducer at the opening of an ultrasonic probe according to a modification of this embodiment.

FIG. 9 is a graph showing a simulation result to be compared with that in FIG. 5, and showing an output signal (80° C.) at the time of transmission of five waves of ultrasonic waves having a frequency of 100 kHz, together with a reference signal (25° C.) according to the modification of this embodiment.

FIG. 10 is a graph showing a simulation result to be compared with that in FIG. 5, and showing an output signal (80° C.) at the time of transmission of five waves of ultrasonic waves having a frequency of 10 MHz, together with a reference signal (25° C.) according to the modification of this embodiment.

FIG. 11 is a sectional view of a conventional ultrasonic probe in the lens direction.

FIG. 12 is a sectional view of the conventional ultrasonic probe in the array direction.

FIG. 13 is a sectional view of a conventional ultrasonic probe having a thermistor in the array direction.

DETAILED DESCRIPTION

Figure 2:
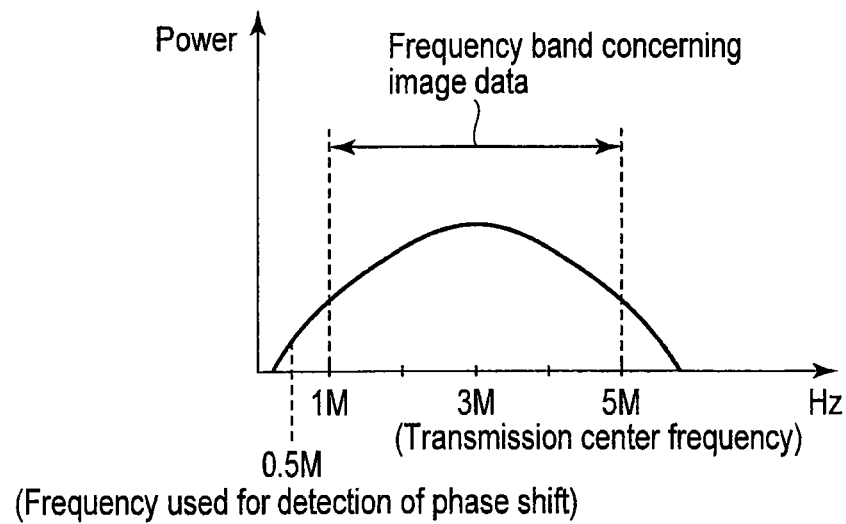
FIG. 2 is a graph showing an example of a power spectrum showing a transmission center frequency and a frequency band concerning image data, together with a frequency used for the detection of a phase shift, according to this embodiment.

In general, according to one embodiment, an ultrasonic diagnostic apparatus includes an ultrasonic probe, a transmission/reception unit, an image generation unit, a control unit, and a phase shift detection unit. The ultrasonic probe has a laminated structure including an acoustic matching layer, a transducer layer having a plurality of arrayed transducers, and a backing layer. The transmission/reception unit is configured to transmit and receive ultrasonic waves to and from an object via the transducers. The image generation unit is configured to generate image data based on an output from the transmission/reception unit. The control unit is configured to control the transmission/reception unit to synchronize generation of ultrasonic waves by a specific transducer out of the plurality of transducers, with reception of ultrasonic waves by a transducer different from the specific transducer. The phase shift detection unit is configured to detect a phase shift of an output signal from the transmission/reception unit to reference signal, the output signal corresponding to synchronization between the generation of ultrasonic waves and the reception of ultrasonic waves.

An ultrasonic diagnostic apparatus according to this embodiment will be described below with reference to the accompanying drawing. Note that the same reference numerals denote constituent elements having almost the same arrangements in the following description, and a repetitive description will be made only when required.

FIG. 1 is a block diagram showing the arrangement of an ultrasonic diagnostic apparatus 1 according to this embodiment. As shown in FIG. 1, the ultrasonic diagnostic apparatus 1 includes an ultrasonic probe 11, an apparatus main body 12, an input device 13 connected to the apparatus main body 12 to input various instructions, commands, and information from the operator to the apparatus main body 12, and a monitor 14. In addition, a biological signal measurement unit (not shown) typified by an electrocardiograph, phonocardiograph, sphygmograph, or respiration sensor and a network may be connected to the ultrasonic diagnostic apparatus 1 via an interface unit 37.

The ultrasonic probe 11 includes a transducer layer having a plurality of transducers, a plurality of acoustic matching layers, and a backing material provided on the rear surface side of the transducer layer. The plurality of transducers are reversible acoustic/electric conversion elements such as piezoelectric ceramic elements. The plurality of transducers are juxtaposed and mounted on the distal end of the ultrasonic probe 11. The plurality of acoustic matching layers are stacked in front of the transducer layer. For the sake of simplicity, assume that there are three types of acoustic matching layers. More specifically, the first acoustic matching layer is stacked on the ultrasonic emitting surface side (to be referred to as an emitting surface side hereinafter) of the transducer layer. The second acoustic matching layer is stacked on the emitting surface side of the first acoustic matching layer. The third acoustic matching layer is stacked on the emitting surface side of the second acoustic matching layer. Note that at least one of the plurality of acoustic matching layers is not segmented for the plurality of transducers. For example, the first and second acoustic matching layers are segmented in accordance with the plurality of transducers on the transducer layer. The third acoustic matching layer has a non-segmented structure for the plurality of transducers on the transducer layer.

If the plurality of transducers are arrayed one-dimensionally (to be referred to as one-dimensional array transducers hereinafter), an acoustic lens is disposed on the emitting surface side of the third acoustic matching layer. If the plurality of transducers are arrayed two-dimensionally (to be referred to as two-dimensional array transducers hereinafter), no acoustic lens is required. A common electrode is disposed between the piezoelectric transducers and the acoustic lens.

The backing material prevents ultrasonic waves from propagating backward from the transducers. An FPC (Flexible Printed Circuit) having a plurality of individual electrodes respectively corresponding to a plurality of transducers is disposed between the transducer layer and the backing material. The FPC is connected to the transmission/reception unit (to be described later) of the apparatus main body 12 via a cable from the ultrasonic probe 11. Assume that in the following description, one transducer forms one channel.

Each of the plurality of transducers generates an ultrasonic wave in response to a driving signal supplied from the pulser of a transmission/reception unit 20 (to be described later). When the ultrasonic probe 11 transmits an ultrasonic wave to an object P, the transmitted ultrasonic wave (to be referred to as the transmission ultrasonic wave hereinafter) is sequentially reflected by a discontinuity surface of acoustic impedance of living tissue in the object. Each transducer receives the reflected ultrasonic waves and generates an echo signal. The amplitude of this echo signal depends on an acoustic impedance difference on the discontinuity surface, as a boundary, by which the echo signal is reflected. The frequency of the echo signal produced when a transmission ultrasonic wave is reflected by a moving blood flow, the surface of the cardiac wall, or the like is subjected to a frequency shift depending on the velocity component of the moving body (the blood flow and the surface of the cardiac wall) in the ultrasonic transmission direction due to the Doppler effect.

The ultrasonic probe 11 will be described below as a probe designed to perform two-dimensional scanning with a one-dimensional array. Note that the ultrasonic probe 11 may be a mechanical four-dimensional probe which executes three-dimensional scanning by swinging a one-dimensional array in a direction perpendicular to the array direction of a plurality of transducers. In addition, the ultrasonic probe 11 is not limited to a mechanical four-dimensional probe, and it is possible to use a two-dimensional array probe having two-dimensional array transducers.

The apparatus main body 12 includes the transmission/reception unit 20, an HPF (High Pass Filter) 23, an LPF (Low Pass Filter) 25, a phase shift detection unit 27, a temperature estimation unit 29, an image generation unit 31, an image combining unit 33, a storage unit 35, the interface unit 37, and a CPU (Central Processing Unit) 39.

The transmission/reception unit 20 includes a rate pulse generator 21A, a transmission delay circuit 21B, a pulser circuit 21C corresponding to each of a plurality of channels, a preamplifier 22A, an A/D (Analog to Digital) converter (not shown), a reception delay circuit 22B, and an adder 22C. The transmission/reception unit 20 supplies a driving signal to each of the plurality of transducers of the ultrasonic probe 11 under the control of the CPU 39.

The rate pulse generator 21A repeatedly generates rate pulses for the formation of transmission ultrasonic waves at a predetermined rate frequency fr Hz (period: 1/fr sec). The generated rate pulses are distributed in number corresponding to a channel count and sent to the transmission delay circuit 21B. The transmission delay circuit 21B gives each rate pulse a delay time (to be referred to as a transmission delay time hereinafter) necessary to focus a transmission ultrasonic wave into a beam and determine transmission directivity for each of the plurality of channels. The storage unit 35 (to be described later) stores the transmission direction or transmission delay time of transmission ultrasonic waves (to be referred to as a transmission delay pattern hereinafter). The CPU 39 (to be described later) refers to the transmission delay pattern stored in the storage unit 35 at the time of transmission of ultrasonic waves. The pulser circuit 21C applies a voltage pulse (driving signal) to each of the plurality of transducers of the ultrasonic probe 11 at the timing based on this rate pulse. With this operation, an ultrasonic beam is transmitted to the object.

The preamplifier 22A amplifies an echo signal received from the object P via the ultrasonic probe 11 for each channel. The A/D converter converts each amplified echo signal into a digital signal. The reception delay circuit 22B gives the echo signals converted into digital signals delay times (to be referred to as reception delay times hereinafter) required to determine reception directivity. The storage unit 35 (to be described later) stores the reception direction or reception delay time of an echo signal (to be referred to as a reception delay pattern hereinafter). The CPU 39 (to be described later) refers to the reception delay pattern stored in the storage unit 35 at the time of reception of ultrasonic waves.

The adder 22C adds a plurality of echo signals given the delay times. With this addition, the transmission/reception unit 20 generates a reception signal (to be also referred to as an RF (radiofrequency) signal) with a reflection component from a direction corresponding to the reception directivity being enhanced. The transmission directivity and the reception directivity determine the comprehensive directivity of ultrasonic transmission/reception. This comprehensive directivity determines an ultrasonic beam (so-called "ultrasonic scanning line"). Note that a digital beam former may be used in place of the preamplifier 22A, the A/D converter, and the reception delay circuit 22B.

The transmission/reception unit 20 synchronizes the generation of ultrasonic waves by a specific transducer of the plurality of transducers with the reception of ultrasonic waves by a transducer (to be referred to as a reception transducer hereinafter) different from the specific transducer under the control of the CPU 39 (to be described later). The transmission/reception unit 20 synchronizes the generation of ultrasonic waves and the reception of ultrasonic waves every time, for example, a scan range is scanned. Note that the transmission/reception unit 20 may synchronize the generation of ultrasonic waves and the reception of ultrasonic waves for each ultrasonic transmission/reception corresponding to one scanning line in the scan range. Note that a reception transducer may be a transducer adjacent to a specific transducer (to be referred to as an adjacent element hereinafter).

The transmission/reception unit 20 may synchronize the generation of ultrasonic waves and the reception of ultrasonic waves for two transducers spaced from each other by a predetermined interval (to be referred to as a transducer pair hereinafter). At this time, the predetermined interval is decided based on the attenuation amount of transverse waves of ultrasonic waves propagating in the third acoustic matching layer and the arrival time of reflected waves of ultrasonic waves by the acoustic lens surface at a transducer for reflected waves of acoustic waves on the acoustic lens surface. The predetermined interval is, for example, a distance corresponding to one to two transducers. Note that this apparatus may include a plurality of transducer pairs. At this time, the temperature estimation unit 29 (to be described later) can estimate the temperature distribution of the third acoustic matching layer. The apparatus may include one specific transducer or a plurality of reception transducers. In addition, a reception transducer can be set at an arbitrary position at the opening.

The transmission/reception unit 20 applies, to a specific transducer, a voltage which has a frequency that does not influence an ultrasonic image (to be described above) and is used to generate ultrasonic waves having a frequency close to the resonance frequency (natural frequency) of transverse waves of the third acoustic matching layer. The ultrasonic waves generated by a specific transducer after scanning on the scan range with ultrasonic waves has a wave number that tends to make ultrasonic waves from the third acoustic matching layer propagate as transverse waves, an PRF (Pulse Repetition Frequency), and the above frequency.

The transmission/reception unit 20 receives transverse waves of ultrasonic waves propagating in the third acoustic matching layer via a reception transducer in synchronism with the generation of ultrasonic waves by a specific transducer under the control of the CPU 39 (to be described later). More specifically, the non-segmented acoustic matching layer converts the ultrasonic waves generated by the specific transducer into transverse waves. The transverse waves propagate in the non-segmented acoustic matching layer in a direction (to be referred to as an orthogonal direction hereinafter) perpendicular to the radiation direction of ultrasonic waves (to be referred to as an acoustic radiation direction hereinafter). The transverse waves propagating in the non-segmented acoustic matching layer reach the reception transducer. The transmission/reception unit 20 outputs an output signal from the reception transducer to the LPF 25 (to be described later).

FIG. 2 is a graph concerning a frequency spectrum, which shows a transmission frequency of 3 MHz and the frequency band of 1 MHz to 5 MHz which is used for imaging, together with a frequency concerning an output signal concerning the detection of a phase shift (to be described later). The transmission frequency of ultrasonic waves concerning imaging will be referred to as an imaging transmission frequency hereinafter.

The HPF 23 is a digital filter which passes high-frequency components (in the frequency band of 1 MHz to 5 MHz in FIG. 2), out of the reception signal output from the transmission/reception unit 20, which concern imaging. The reception signal passing through the HPF 23 is output to the image generation unit 31 (to be described later). Note that the HPF 23 cuts off the output signal output from the transmission/reception unit 20 which corresponds to the synchronization between the generation of ultrasonic waves and the reception of ultrasonic waves.

The LPF 25 is a digital filter which passes low-frequency components (in the frequency band of 1 MHz or less in FIG. 2), out of the reception signal output from the transmission/reception unit 20, which concern the detection of a phase shift (to be described later). More specifically, the LPF 25 passes the output signal from the transmission/reception unit 20 which corresponds to the synchronization between the generation of ultrasonic waves and the reception of ultrasonic waves. The output signal from the transmission/reception unit 20 which corresponds to the synchronization between the generation of ultrasonic waves and the reception of ultrasonic waves is the signal output from the reception transducer (to be referred to as a transverse wave reception signal hereinafter) which is output upon reception of the transverse waves of the ultrasonic waves which have propagated in the acoustic matching layer. The LPF 25 cuts off a reception signal concerning imaging.

Note that the HPF 23 and the LPF 25 may be filters designed to switch frequency bands that can pass, in synchronism with the reception of ultrasonic waves for the detection of a phase shift and the reception of ultrasonic waves for imaging.

Figure 3:
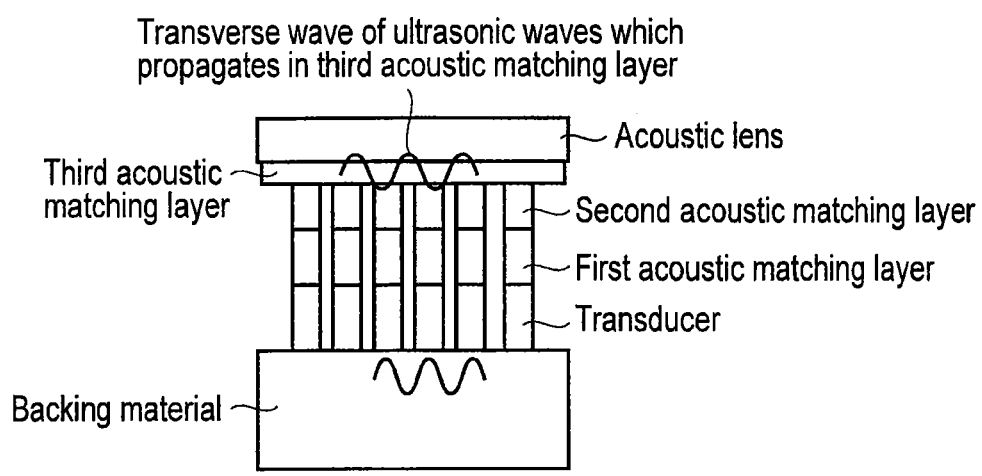
FIG. 3 is a schematic view showing an example of an outline of a transverse wave of ultrasonic waves which propagates in an acoustic matching layer according to this embodiment.

FIG. 3 is a sectional view of the ultrasonic probe 11 in the array direction, showing an example of a transverse wave of ultrasonic waves which propagates in the third acoustic matching layer. In the process of propagating in the probe, some of ultrasonic waves are converted into a transverse wave by the non-segmented acoustic matching layer. The transverse wave propagating in the acoustic radiation direction also propagates in the direction perpendicular to the acoustic radiation direction and reaches an adjacent element.

The phase shift detection unit 27 detects a phase shift relative to a reference signal for an output signal (transverse wave reception signal) passing through the LPF 25. More specifically, the phase shift detection unit 27 reads out the reference signal stored in the storage unit 35 (to be described later) from the storage unit 35. The phase shift detection unit 27 detects a phase shift of a transverse wave reception signal relative to the reference signal. A phase shift is, for example, the interval (to be referred to as the time interval hereinafter) between the time corresponding to the maximum amplitude of the reference signal at a predetermined wave number and the time corresponding to the maximum amplitude of the transverse wave reception signal at the same wave number as the predetermined wave number. The reference signal is, for example, an output signal from the transmission/reception unit 20 which corresponds to the synchronization between the generation of ultrasonic waves by a specific transducer and the reception of ultrasonic waves by a reception transducer when the temperature of the third acoustic matching layer is 25° C. The phase shift detection unit 27 outputs the detected phase shift to the CPU 39 and the temperature estimation unit 29 (both of which will be described later).

The phase shift detection unit 27 can detect a plurality of phase shifts respectively corresponding to a plurality of transducer pairs. The phase shift detection unit 27 outputs a plurality of phase shifts to the CPU 39 and the temperature estimation unit 29 (both of which will be described later).

Figure 4:
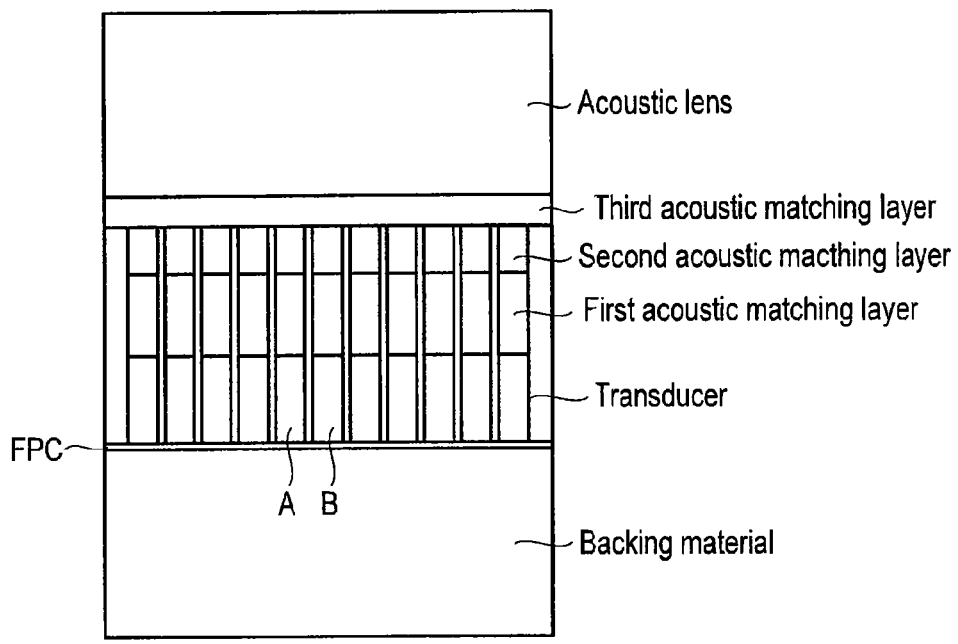
FIG. 4 is a view showing an example of a calculation model for an ultrasonic probe used for FEM according to this embodiment.
Figure 5:
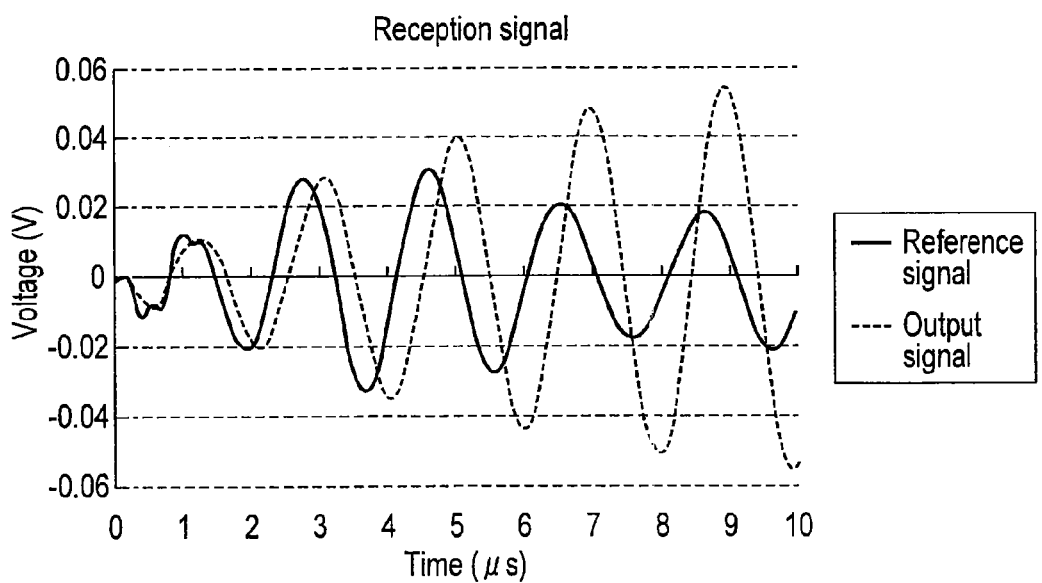
FIG. 5 is a graph showing the simulation result obtained by using the calculation model in FIG. 4, and showing an output signal (80° C.) at the time of transmission of five waves of ultrasonic waves having a frequency of 500 kHz, together with a reference signal (25° C.), according to this embodiment.

FIG. 4 is a view showing an example of a calculation model in computer simulation by an FEM (Finite Element Method). Assume that a selector array probe with a center frequency of about 3 MHz is used as a calculation model. Referring to FIG. 4, reference symbol A denotes a specific transducer; and B, a reception transducer. FIG. 5 is a view showing an example of the simulation result obtained by the FEM using the calculation model in FIG. 4. The transmission frequency of ultrasonic waves is 500 kHz, and the wave number is 5. Referring to FIG. 5, the solid line indicates the waveform of a reference signal when the temperature of the third acoustic matching layer is 25° C. which is close to that in a normal use state. Referring to FIG. 5, the dotted line indicates the waveform of an output signal (transverse wave reception signal) when the temperature of the third acoustic matching layer is 80° C., which clearly indicates an abnormal heat generation state. Since the sound velocity changes depending on the temperature of a material used for an acoustic matching layer, calculations were performed upon specifying of sound velocities at the respective temperatures in this simulation. The time interval sandwiched between the arrows in FIG. 5 indicates a phase shift between the time corresponding to the maximum amplitude value of a reference signal and the time corresponding to the maximum amplitude value of a transverse wave reception signal.

Note that FIG. 6 is a view showing an example of the simulation result obtained by the FEM using the calculation model in FIG. 4. The transmission frequency corresponds to a wave number of 5 at 3 MHz. Referring to FIG. 6, the solid line indicates the waveform of a reference signal when the temperature of the third acoustic matching layer is 25° C. Referring to FIG. 6, the dotted line indicates the waveform of an output signal (transverse wave reception signal) when the temperature of the third acoustic matching layer is 80° C. As shown in FIG. 6, when the transmission frequency is 3 MHz, no phase shift can be detected.

The LPF 25 cuts off reception signals having frequencies higher than the minimum frequency of a frequency band concerning image data in FIG. 2, and passes output signals having frequencies lower than the minimum frequency of the frequency band in FIG. 2. The HPF 23 passes reception signals in the frequency band concerning image data in FIG. 2.

The temperature estimation unit 29 reads out a correspondence table (to be referred to as matching layer temperature correspondence table hereinafter) of phase shifts corresponding to the temperatures of the third acoustic matching layer from the storage unit 35 (to be described later). The temperature estimation unit 29 estimates the temperature of the third acoustic matching layer based on the phase shift output from the phase shift detection unit 27 and the matching layer temperature correspondence table. The temperature estimation unit 29 outputs the estimated temperature to the image combining unit 33 (to be described later). Note that the temperature estimation unit 29 may output the estimated temperature to the CPU 39 and the monitor 14 (both of which will be described later). The temperature estimation unit 29 can also estimate the temperature distribution of the third acoustic matching layer based on a plurality of phase shifts respectively corresponding to a plurality of transducers and the matching layer temperature correspondence table.

In addition, the temperature estimation unit 29 reads out a correspondence table (to be referred to as a contact surface temperature correspondence table hereinafter) of the temperatures of the contact surface between the ultrasonic probe 11 and the object in association with the temperatures of the third acoustic matching layer from the storage unit 35. The temperature estimation unit 29 estimates the temperature of the contact surface based on the estimated temperature of the third acoustic matching layer and the contact surface temperature correspondence table. The temperature estimation unit 29 outputs the estimated temperature of the contact surface to the image combining unit 33 (to be described later). Note that the temperature estimation unit 29 can estimate the temperature distribution of the contact surface based on the temperature distribution of the third acoustic matching layer and the matching layer temperature correspondence table. The temperature estimation unit 29 outputs the estimated temperature distribution to the image combining unit 33 (to be described later).

The image generation unit 31 includes a B-mode processing unit, Doppler processing unit, and image generation unit (none of which are shown). The image generation unit 31 generates an ultrasonic image. Ultrasonic images include B-mode images and Doppler images (which will be described later).

The B-mode processing unit includes an envelope detector and a logarithmic converter (neither of which is shown). The envelope detector performs envelope detection of the reception signal output from the HPF 23. The envelope detector outputs the envelope-detected signal to the logarithmic converter (to be described later). The logarithmic converter relatively enhances a weak signal by logarithmically converting the envelope-detected signal. The B-mode processing unit generates a signal value (B-mode data) for each depth on each scanning line or in each ultrasonic transmission/reception based on the signal enhanced by the logarithmic converter.

The B-mode processing unit generates three-dimensional B-mode data having a plurality of signal values respectively arranged in the azimuth direction, elevation direction, and depth direction (to be referred to as the range direction hereinafter) in a scanned region. The range direction is the depth direction on a scanning line. The azimuth direction is, for example, an electronic scanning direction along the array direction of one-dimensional ultrasonic transducers. The elevation direction is the mechanical swinging direction of the one-dimensional ultrasonic transducers.

Note that three-dimensional B-mode data may be data obtained by arranging a plurality of pixel values, a plurality of luminance values, or the like in the azimuth direction, elevation direction, and range direction, respectively, along scanning lines. In addition, three-dimensional B-mode data may be data concerning an ROI (Region Of Interest) set in advance in a scanned region. The B-mode processing unit may generate volume data instead of three-dimensional B-mode data. The date generated by the B-mode processing unit will be collectively referred to as B-mode data.

The Doppler processing unit includes a mixer, low pass filter, and velocity/variance/power computation device (none of which are shown). The mixer multiplies the reception signal output from the HPF 23 by a reference signal having a frequency $f_0$ equal to the transmission frequency. This multiplication obtains a signal having a component with a Doppler shift frequency $f_d$ and a signal having a frequency component of $(2f_0+f_d)$. The low pass filter removes a signal of a high-frequency component $(2f_0+f_d)$ from a signal having two types of frequency components from the mixer. Removing the signal of the high-frequency component $(2f_0+f_d)$ will generate a Doppler signal having the component with the Doppler shift frequency $f_d$.

Note that the Doppler processing unit may use a quadrature detection scheme to generate Doppler signals. In this case, the Doppler processing unit performs quadrature detection to convert a reception signal (RF signal) into IQ signals. A Doppler processing unit 142 generates a Doppler signal having the Doppler shift frequency $f_d$ by performing complex Fourier transform on the IQ signals. Doppler signals are, for example, echo components due to a blood flow, tissue, and contrast medium.

The velocity/variance/power computation device includes an MTI (Moving Target Indicator) filter and an autocorrelation computation unit (neither of which is shown). The MTI filter removes a Doppler component (a clutter component) due to the respiratory movement or pulsatory movement of an organ or the like from a generated Doppler signal. The autocorrelation computation unit calculates the autocorrelation value of the Doppler signal obtained by extracting only blood flow information using the MTI filter. The autocorrelation computation unit calculates the average flow velocity value, a variance, the reflection intensity of the Doppler signal, and the like on the basis of the calculated autocorrelation value. The velocity/variance/power computation device generates color Doppler data from the average velocity value, the variance, the reflection intensity of the Doppler signal, and the like based on a plurality of Doppler signals. Doppler signals and color Doppler data will be collectively referred to as Doppler data hereinafter.

In addition, Doppler data and B-mode data will be collectively referred to as raw data. Note that raw data of an echo signal may be B-mode data based on harmonic components of transmission ultrasonic waves and elastic data concerning living tissue in the object. The B-mode processing unit and the Doppler processing unit output the generated raw data to the image generation unit. Note that B-mode processing unit and the Doppler processing unit can also output the generated raw data to a cine memory (not shown).

The image generation unit includes a DSC (Digital Scan Converter) (not shown). The image generation unit executes coordinate conversion processing (resampling) for the DSC. Coordinate conversion processing is to convert, for example, a scanning line signal string for ultrasonic scanning, which is formed from raw data, into a scanning line signal string in a general video format typified by a TV format. The image generation unit executes interpolation processing following coordinate conversion processing for the DSC. Interpolation processing is to interpolate data between scanning line signal strings by using raw data in the adjacent scanning line signal strings.

The image generation unit generates an ultrasonic image as a display image by executing coordinate conversion processing and interpolation processing for raw data. Note that the image generation unit may include an image memory storing data (to be referred to as image data hereinafter) corresponding to the generated ultrasonic image. The image generation unit outputs the raw data obtained by executing coordinate conversion processing and interpolation processing to the image combining unit 33. The ultrasonic image generated by using B-mode data will be referred to as B-mode image hereinafter. In addition, an ultrasonic image generated by using Doppler data will be referred to as a Doppler image.

A cine memory is a memory which stores ultrasonic images corresponding to a plurality of frames immediately before freezing. Continuously displaying (cine displaying) the images stored in this cine memory can display a moving ultrasonic image.

The image combining unit 33 combines a generated ultrasonic image with the character information of various parameters, scale marks, and the like. The image combining unit 33 outputs the combined ultrasonic image to the monitor 14. The image combining unit 33 can also combine the temperature (at least one of the temperature of the contact surface and the temperature of the third acoustic matching layer) estimated by the temperature estimation unit 29 with an ultrasonic image to output the resultant image to the monitor 14 (to be described later). The image combining unit 33 can also combine the temperature distribution estimated by the temperature estimation unit 29 with an ultrasonic image to output the resultant image to the monitor 14 (to be described later).

The storage unit 35 stores pluralities of reception delay patterns and transmission delay patterns with different focus depths, control programs for the ultrasonic diagnostic apparatus 1, a diagnostic protocol, various data groups such as transmission/reception conditions, the raw data and ultrasonic images generated by the image generation unit 31, and the like. The storage unit 35 stores a matching layer temperature correspondence table. The storage unit 35 stores predetermined thresholds. A predetermined threshold is, for example, the value of a phase shift corresponding to the temperature of the third acoustic matching layer. A predetermined threshold is the value of a phase shift corresponding to a temperature concerning safety for an object (to be referred to as a limit temperature). Note that the storage unit 35 may store predetermined warnings, predetermined warning sounds, and the like (which will be described later). The storage unit 35 may also store a limit temperature. The storage unit 35 may store a contact surface temperature correspondence table.

The interface unit 37 is an interface concerning the input unit 13, a network, an external storage device (not shown), and a biological signal measurement unit (not shown). Data such as ultrasonic images, analysis results, and the like obtained by the apparatus main body 12 can be transferred to other apparatuses via the interface unit 37 and the network. The interface unit 37 can also download the medical images concerning the object which are acquired by other medical image diagnostic apparatuses (not shown) via the network.

The CPU 39 reads out a transmission delay pattern, reception delay pattern, and apparatus control program stored in the storage unit 35 based on the selection between the B mode and the Doppler mode, frame rate, scan depth, and transmission start/end which are input by the operator via the input device 13, and controls the apparatus main body 12 and the ultrasonic probe 11 in accordance with these piece of information. The CPU 39 controls the transmission/reception unit 20 to establish synchronization between the generation of ultrasonic waves by a specific transducer of a plurality of transducers and the reception of ultrasonic wave by a transducer different from the specific transducer. The CPU 39 reads out a predetermined threshold stored in the storage unit 35. If a detected phase shift reaches the predetermined threshold, the CPU 39 controls the transmission/reception unit 20 to decrease a voltage (to be referred to as an application voltage hereinafter) to be applied to a transducer so as to generate ultrasonic waves concerning the generation of image data.

If the phase shift detection unit 27 outputs a plurality of phase shifts respectively corresponding to a plurality of transducer pairs, the CPU 39 may compare the maximum phase shift among the plurality of phase shifts with a predetermined threshold. Alternatively, the CPU 39 may select a phase shift concerning a reception transducer closest to the opening center among the plurality of transducer pairs and compare the selected phase shift with a predetermined threshold.

Note that when a detected phase shift reaches a predetermined threshold, the CPU 39 may execute the following control. The CPU 39 controls the transmission/reception unit 20 to stop applying application voltages to the transducers. The CPU 39 can also control the monitor 14 to display a predetermined warning on the monitor. The CPU 39 may control an audio output unit (not shown) to output a predetermined warning sound from the audio output unit.

More specifically, when a detected phase shift reaches a predetermined threshold, the CPU 39 reads out a predetermined warning stored in the storage unit 35 from the storage unit 35. The CPU 39 causes the monitor 14 (to be described later) to display the readout predetermined warning.

In addition, when the detected phase shift reaches the predetermined threshold, the CPU 39 reads out the predetermined warning sound stored in the storage unit 35 from the storage unit 35. The CPU 39 then causes the audio output unit (to be described later) to output the readout predetermined warning sound.

Note that the CPU 39 may compare an estimated temperature with the limit temperature stored in the storage unit 35. At this time, when the estimated temperature reaches the limit temperature, the CPU 39 controls the transmission/reception unit 20 to decrease a voltage (to be referred to as an application voltage hereinafter) to be applied to a transducer or to stop applying an application voltage to the transducer.

The input device 13 is connected to the interface unit 37 and inputs various instructions, commands, information, selections, and settings from the operator to the apparatus main body 12. The input device 13 includes input devices such as a trackball, switch buttons, mouse, and keyboard (none of which are shown). The input device detects the coordinates of a cursor displayed on the display screen, and outputs the detected coordinates to the CPU 39. Note that the input device may be a touch command screen provided to cover the display screen. In this case, the input device 13 detects a touched and designated coordinates by a coordinate reading principle such as an electromagnetic induction scheme, magnetostriction scheme, or a pressure-sensitive scheme, and outputs the detected coordinates to the CPU 39. When, for example, the operator operates the end button or freeze button of the input device 13, the ultrasonic transmission/reception is terminated, and the apparatus main body 12 is set in a pause state.

The output unit (not shown) includes the monitor 14 (to be described later) and the audio output unit (not shown). The monitor 14 displays a predetermined warning under the control of the CPU 39, when a detected phase shift reaches the predetermined threshold. The audio output unit (not shown) outputs a predetermined warning sound under the control of the CPU 39, when a detected phase shift reaches the predetermined threshold.

The monitor 14 displays ultrasonic images such as a B-mode image and a Doppler image based on outputs from the image combining unit 33. Note that the monitor 14 may execute adjustments concerning brightness, contrast, dynamic range, γ correction, and the like and color mapping. Note that the monitor 14 can display at least one of the temperature of the contract surface and the temperature of the third acoustic matching layer. The monitor 14 can display the temperature distribution of the third acoustic matching layer or the temperature distribution of the contact surface.

(Phase Shift Transmission/Reception Control Function)

The phase shift transmission/reception control function is a function of controlling the transmission/reception of ultrasonic waves based on a detected phase shift and a predetermined threshold. Processing concerning the phase shift transmission/reception control function (to be referred to as phase shift transmission/reception control processing hereinafter) will be described below.

FIG. 7 is a flowchart showing a procedure for the phase shift transmission/reception control processing.

The apparatus transmits ultrasonic waves to an object and generates a B-mode image (step Sa1). A specific transducer generates ultrasonic waves (step Sa2). The apparatus generates a transverse wave reception signal via a reception transducer in synchronism with the generation of ultrasonic waves by a specific transducer (step Sa3). The apparatus detects a phase shift of the transverse wave reception signal relative to the reference signal (step Sa4). If the detected phase shift is less than a predetermined threshold, the apparatus repeats the processing from step Sa1 to step Sa4 (step Sa5). If the detected phase shift is equal to or more than the predetermined threshold, the apparatus stops transmitting ultrasonic waves to the object (step Sa6).

If the detected phase shift is equal to or more than the predetermined threshold, the apparatus may output at least one of a predetermined warning and a predetermined warning sound from the output unit. More specifically, if the detected phase shift is equal to or more than the predetermined threshold, the apparatus may execute at least one of the following operations: displaying a predetermined warning on the monitor 14 and outputting a predetermined warning sound from the audio output unit.

Note that the apparatus estimates the temperature of an acoustic matching layer by using a detected phase shift and can stop transmitting ultrasonic waves to the object based on the estimated temperature and the limit temperature. The storage unit 35 stores the data of the limit temperature. More specifically, the apparatus estimates the temperature of the third acoustic matching layer based on the phase shift and the correspondence table. The apparatus compares the estimated temperature with the limit temperature read out from the storage unit. In this case, if the estimated temperature is less than the limit temperature, the apparatus repeats the processing from step Sa1 to step Sa4. If the estimated temperature is equal to or more than the limit temperature, the apparatus stops transmitting ultrasonic waves to the object.

(Modification)

This modification differs from the embodiment in that it includes a transducer (to be referred to as the first transducer hereinafter) which generates ultrasonic waves having a transmission center frequency (to be referred to as a phase shift detection frequency hereinafter) used for the detection of a phase shift, a transducer (to be referred to as the second transducer hereinafter) which receives transverse waves of ultrasonic waves propagating in the third acoustic matching layer, and a plurality of transducers (to be referred to as the third transducers hereinafter) which generate ultrasonic waves to be transmitted to the object to generate an ultrasonic image and receive ultrasonic waves reflected by the interior of the object and generate echo signals. Note that the first and second transducers may be transducers having the same structure. The first and second transducers are transducers dedicated for the detection of a phase shift. The third transducer is a dedicated transducer concerning the generation of an ultrasonic image.

The first transducer is located in the opening center of the ultrasonic probe. Note that the first transducer may be located near the opening center. The opening center is, for example, the center of gravity of an opening shape. The second transducer is placed near the first transducer. More specifically, the second transducer is placed adjacent to the first transducer. Note that the second transducer may be spaced apart from the first transducer by a predetermined interval. In addition, pluralities of first and second transducers may be arranged in pairs.

If, for example, the first transducer has an imaging transmission frequency of 3 MHz, the transducer generates ultrasonic waves having a frequency of 500 kHz as a phase shift detection frequency under the control of the CPU 39. A phase shift detection frequency is decided in advance by, for example, a computer simulation using the material of the third acoustic matching layer. The material and thickness of the first transducer are decided to efficiently generate the decided phase shift detection frequency.

FIG. 8 is a view showing an example of an opening in the ultrasonic emitting surface of the ultrasonic probe 11 having two-dimensional array transducers and the arrangement of the first to third transducers at the opening. To show the positions of the first to third transducers at the opening, the illustration of the first to third acoustic matching layers is omitted. Referring to FIG. 8, reference symbol A denotes the first transducer; and B, the second transducer.

FIG. 9 is a graph showing an example of the simulation result obtained by the FEM using the calculation model in FIG. 4. The phase shift detection frequency of ultrasonic waves generated by the first transducer is 100 kHz, and the wave number is 5. Referring to FIG. 9, the solid line indicates the waveform of a reference signal when the temperature of the third acoustic matching layer is 25° C. Referring to FIG. 9, the dotted line indicates the waveform of an output signal (transverse wave reception signal) when the temperature of the third acoustic matching layer is 80° C. FIG. 9 indicates that when the phase shift detection frequency is 100 kHz, no phase shift can be detected.

FIG. 10 is a view showing an example of the simulation result obtained by the FEM using the calculation model in FIG. 4. The phase shift detection frequency of ultrasonic waves generated by the first transducer is 10 MHz, and the wave number is 5. Referring to FIG. 10, the solid line indicates the waveform of a reference signal when the temperature of the third acoustic matching layer is 25° C. Referring to FIG. 10, the dotted line indicates the waveform of an output signal (transverse wave reception signal) when the temperature of the third acoustic matching layer is 80° C. FIG. 10 indicates that when the phase shift detection frequency is 10 MHz, no phase shift can be detected.

According to the above arrangement, the following effects can be obtained.

The ultrasonic diagnostic apparatus 1 can cause a specific transducer to generate, for each scanning on a scan range concerning an ultrasonic image, ultrasonic waves having a frequency, wave number, and PRF that allow easy propagation in a non-segmented acoustic matching layer like the third acoustic matching layer and have no influence on a generated ultrasonic image. The ultrasonic diagnostic apparatus 1 can synchronize the generation of ultrasonic waves by a specific transducer with the reception of ultrasonic waves by a transducer different from the specific transducer and detect a phase shift of an output signal corresponding to the synchronization relative to a reference signal. When a detected phase shift reaches a predetermined threshold, the ultrasonic diagnostic apparatus 1 can control the transmission/reception unit to decrease an application voltage to be applied to a transducer or stop applying an application voltage to the transducer.

With these effects, the ultrasonic diagnostic apparatus 1 can decrease an application voltage or stop applying an application voltage before the temperature of the contact surface between the ultrasonic probe 11 and the object becomes a high temperature, without installing any temperature sensor such as a thermistor or any pressure sensor or any signal line for the extraction of an output from each sensor in the ultrasonic probe 11. The ultrasonic diagnostic apparatus 1 allows a reduction in the manufacturing cost of the ultrasonic probe 11 because it need not install any temperature sensor such as a thermistor or any pressure sensor or install any signal line for the extraction of an output from each sensor in the ultrasonic probe 11. In addition, the ultrasonic diagnostic apparatus 1 can detect a phase shift at an arbitrary position in the opening, and hence can estimate and display the temperature distribution of an acoustic matching layer and the temperature distribution of the contact surface. In addition, the ultrasonic diagnostic apparatus 1 can display a predetermined warning and generate (output) a predetermined warning sound based on a phase shift and a threshold.

According to the modification of the ultrasonic diagnostic apparatus 1, it is possible to install a transducer for detecting a phase shift in the ultrasonic probe 11. This makes it possible to separate a transducer concerning the generation of an ultrasonic image from a transducer used for the detection of a phase shift. It is therefore possible to set ultrasonic transmission/reception conditions optimal for the generation of an ultrasonic image and the detection of a phase shift.

As has been described above, according to the ultrasonic diagnostic apparatus 1, it is possible to provide an ultrasonic diagnostic apparatus which can monitor the temperature of the ultrasonic probe 11, exhibits high performance, and is safe for the object without having any influence on ultrasonic images.

In addition, each function according to each embodiment can be implemented by installing programs for executing the processing in a computer such as a workstation and expanding them in the memory. In this case, the programs which can cause the computer to execute the corresponding techniques can be distributed by being stored in storage media such as magnetic disks (Floppy® disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
    an ultrasonic probe having a laminated structure including acoustic matching layers, a transducer layer comprising a plurality of arrayed transducers, and a backing layer, wherein one of the acoustic matching layers has a non-segmented structure;
    a transmission/reception circuit configured to cause the ultrasonic probe to transmit and receive ultrasonic waves to and from an object via the transducers;
    an image generation circuit configured to generate image data based on an output from the transmission/reception circuit;
    processing circuitry configured to control the transmission/reception circuit to synchronize ultrasonic-wave generation by a specific transducer of the plurality of transducers with ultrasonic-wave reception by a transducer of the plurality of transducers that is different from the specific transducer, wherein the specific transducer is configured to generate transverse waves of a frequency lower than ultrasonic waves transmitted to the object to image the object, and the transverse waves generated by the specific transducer propagate through the one acoustic matching layer with the non-segmented structure, wherein the transducer is configured to detect the generated transverse waves propagated through the one acoustic matching layer and to generate a transverse wave reception signal as an output signal; and
    a phase shift detection circuit configured to detect a phase shift between the output signal and a reference signal, the output signal corresponding to synchronization between the ultrasonic-wave generation and the ultrasonic-wave reception.

2. The apparatus of claim 1, further comprising output circuitry configured to output a predetermined warning when the detected phase shift reaches a predetermined threshold.

3. The apparatus of claim 2, wherein the output circuitry includes at least one of a monitor configured to display the predetermined warning and an audio output circuit configured to output a warning sound corresponding to the predetermined warning.

4. The apparatus of claim 1, wherein the processing circuitry is configured to control the transmission/reception circuit to decrease a voltage applied to the transducers or stop applying the voltage to the transducers when the detected phase shift reaches a predetermined threshold.

5. The apparatus of claim 1, further comprising a temperature estimation circuit configured to estimate a temperature of the one acoustic matching layer based on dependence of the phase shift on the temperature of the one acoustic matching layer.

6. The apparatus of claim 1, wherein the phase shift detection circuit is configured to detect the phase shift as a time interval.

7. The apparatus of claim 1, wherein the processing circuitry is further configured to control the transmission/reception circuit to synchronize the ultrasonic-wave generation with the ultrasonic-wave reception in a phase different from transmission/reception of ultrasonic waves for the image data.

8. The apparatus of claim 1, further comprising a low pass filter configured to extract the output signal from outputs from the transmission/reception circuit.

* * * * *